United States Patent
Jean (10) Patent No.: US 10,782,280 B2
(45) Date of Patent: Sep. 22, 2020

(54) METHOD AND SYSTEM FOR EVALUATION OF ENGINE CONDITION

(71) Applicant: PRATT & WHITNEY CANADA CORP., Longueuil (CA)

(72) Inventor: Maurice Jean, Boucherville (CA)

(73) Assignee: PRATT & WHITNEY CANADA CORP., Longueuil (CA)

( * ) Notice: Subject to any disclaimer, the term of this patent is extended or adjusted under 35 U.S.C. 154(b) by 134 days.

(21) Appl. No.: 16/180,412

(22) Filed: Nov. 5, 2018

(65) Prior Publication Data

US 2019/0072536 A1 Mar. 7, 2019

Related U.S. Application Data (63) Continuation of application No. 15/137,841, filed on Apr. 25, 2016, now Pat. No. 10,151,739.

(51) Int. Cl.
*G01M 15/04* (2006.01)
*G01N 33/28* (2006.01)
(Continued)

(52) U.S. Cl.
CPC ....... *G01N 33/2858* (2013.01); *F01D 21/003* (2013.01); *F01D 25/18* (2013.01);
(Continued)

(58) Field of Classification Search
USPC ........................................ 73/114.55, 114.56
See application file for complete search history.

(56) References Cited

U.S. PATENT DOCUMENTS

| 3,751,661 A | 8/1973 | Packer et al. |
| 3,981,584 A | 9/1976 | Guymer |

(Continued)

FOREIGN PATENT DOCUMENTS

| EP | 0672243 | 3/2000 |
| EP | 2485037 | 5/2015 |

(Continued)

OTHER PUBLICATIONS

Noria Corporation, "Using Electron Microscopy in Oil Analysis Applications—Comparing SEM to TEM", 6 pages. http://www.machinerylubrication.com/Read/698/electron-microscopy-sem-oil, Jan. 2005.

(Continued)

*Primary Examiner* — Eric S. McCall
(74) *Attorney, Agent, or Firm* — Norton Rose Fulbright Canada LLP (57) ABSTRACT

There is described herein methods and systems for evaluating a condition of an engine. Fluid sample data obtained from an engine is received and weights are assigned to different data sets of the fluid sample data. The data sets correspond to one or more classes of materials into which particles of the fluid sample are sorted. A characterizing sample signature of the engine is generated based on the data sets. The sample signature is compared to a plurality of reference signatures obtained from reference engines belonging to a common family with the engine. A selection is made from the reference engines for those having a difference between a corresponding signature and the sample signature below a threshold. Historical engine data of the selected reference engines is output as a basis for evaluating the condition of the engine.

20 Claims, 9 Drawing Sheets

(51) Int. Cl.
*F01D 25/18* (2006.01)
*F01D 21/00* (2006.01)
*G01N 23/2252* (2018.01)

(52) U.S. Cl.
CPC ... *G01N 23/2252* (2013.01); *F05D 2260/821* (2013.01); *Y02T 50/671* (2013.01)

(56) References Cited

U.S. PATENT DOCUMENTS

| | | |
|---|---|---|
| 5,517,427 A | 5/1996 | Joyce |
| 5,537,336 A | 7/1996 | Joyce |
| 5,586,161 A | 12/1996 | Russell et al. |
| 5,817,928 A | 10/1998 | Garvey, III et al. |
| 5,982,847 A | 11/1999 | Nelson |
| 6,473,677 B1 | 10/2002 | Hershey et al. |
| 6,598,464 B1 | 7/2003 | Rossi |
| 6,643,570 B2 | 11/2003 | Bangert et al. |
| 6,859,517 B2 | 2/2005 | Wilson et al. |
| 7,184,515 B2 | 2/2007 | Wilson |
| 7,523,615 B2 | 4/2009 | Singh et al. |
| 7,634,913 B2 | 12/2009 | Singh et al. |
| 7,689,368 B2 | 3/2010 | Douglas |
| 7,745,382 B2 | 6/2010 | Sloan |
| 8,522,604 B2 | 9/2013 | Zhe et al. |
| 8,607,621 B2 | 12/2013 | verdegan |
| 8,676,436 B2 | 3/2014 | Raimarckers et al. |
| 8,805,624 B2 | 8/2014 | Uluyol |
| 8,862,433 B2 | 10/2014 | Yerramalla et al. |
| 9,032,803 B2 | 5/2015 | Griffaton |
| 9,244,042 B2 | 1/2016 | Rank |
| 9,897,582 B2 | 2/2018 | Jean et al. |
| 10,151,739 B2 | 12/2018 | Jean |
| 2006/0232267 A1* | 10/2006 | Halalay ............... G01N 33/2888 73/53.05 |
| 2010/0138132 A1 | 6/2010 | Apps et al. |
| 2011/0095190 A1 | 4/2011 | Kommareddy et al. |
| 2012/0330499 A1 | 12/2012 | Scheid et al. |
| 2013/0132034 A1 | 5/2013 | Wilson |
| 2014/0121994 A1 | 5/2014 | Jean et al. |
| 2014/0324363 A1 | 10/2014 | Reinman |
| 2015/0047419 A1 | 2/2015 | Cao et al. |
| 2016/0093481 A1 | 3/2016 | Bick et al. |
| 2016/0370341 A1 | 12/2016 | Jean et al. |
| 2017/0159485 A1 | 6/2017 | Jean et al. |
| 2017/0183016 A1 | 6/2017 | Shah et al. |
| 2018/0136179 A1 | 5/2018 | Jean et al. |
| 2019/0187030 A1* | 6/2019 | Takagi ............... G01M 15/102 |
| 2020/0102851 A1* | 4/2020 | Jean .................. F01D 21/003 |

FOREIGN PATENT DOCUMENTS

| | | |
|---|---|---|
| JP | 10330779 | 12/1998 |
| WO | 2008013597 | 1/2008 |
| WO | 2015025160 | 2/2015 |

OTHER PUBLICATIONS

Golden, "The Determination of Iron Used in Lubricating Oil", Applied Spectroscopy, vol. 25, No. 6, Nov./Dec. 1971, pp. 668-671.

Herguth et al., "Applications of Scanning Electron. Microscopy and Energy Dispersive. Spectroscopy (SEM/EDS). To Practical Tribology Problems", Herguth Laboratories, 9 pages. http://www.herguth.com/technical/sem.pdf.

Vahaoja, "Oil Analysis in Machine Diagnostics", Acta Universitatis Ouluensis: A Scientiae Rerum Naturalium, vol. 458, University of Oulu, 2006, 80 pages.

Whitlock, "X-ray Methods for Monitoring Machinery Condition", Advances in X_ray Analysis, vol. 40, proceedings of the 45th Annual Denver X-ray Conferences, Aug. 1996, 12 pages.

Lukas et al., "Rotrode Filter Spectroscopy, Does It have a Place in Commercial or Military Oil Analysis Laboratory", Spectro Incorporated, Littleton, Massachusetts, 7 pages. http://protechanalytical.com/PDF%20files/RFS-4_98-1.pdf.

Eisentraut et al., "Spectrometrix Oil Analysis: Detecting Engine Failures Before They Occur", Analytical Chemistry, vol. 56, No. 9, Aug. 1984, pp. 1086A-1094A.

Farrant et al., "Effective Condition Monitoring of Aero-Engine Systems Using Automated SEM/EDX and New Diagnostic Routines", 1998, 14 pages.

Amsoil, "Correlation between particle size and engine wear", Technical service bulletin, A-F-2007-07-25, 3 pages. https://www.amsoil.com/techservicesbulletin/Aftermarket/TSB-AF-2007-07-25%20Oil%20filters%20Particle%20Size%20and%20Engine%20Wear.pdf.

Scientific and Techinal Information Center, "Search Report", STIC Database Tracking No. 487946, Jun. 19, 2014, 24 pages.

* cited by examiner

METHOD AND SYSTEM FOR EVALUATION OF ENGINE CONDITION

TECHNICAL FIELD

The present disclosure relates generally to methods and systems for engine condition evaluation using fluid analysis, and more particularly to methods and system for evaluating the condition of an engine through an engine fluid signature.

BACKGROUND OF THE ART

The analysis of engine oil or other lubricant for the purpose of identifying premature component wearing has been performed for several decades using optical atomic spectroscopy (e.g., atomic emission spectroscopy (AES), as well as atomic absorption spectroscopy (AAS)). This technology was the basis for the military aviation's Spectroscopic Oil Analysis Program (SOAP). However, it has certain disadvantages, such as a lack of repeatability among different equipment and an inability to analyze particles greater than 5 µm in diameter. Furthermore, optical atomic spectroscopy is an elemental analysis of the total oil sample and typically does not characterize individual particles in the sample.

Other approaches have since been proposed, whereby diagnosis of an engine condition is based on the identification of a pattern that can be associated with a component failure. However, these approaches are limited when the failure mechanism is unknown.

Therefore, there is room for improvement.

SUMMARY

There is described herein methods and systems for comparing an engine fluid signature of a first engine with engine fluid signatures of other engines of a same engine family. A delta signature is obtained via the comparison and delta signatures below a given threshold are considered similar. Historical data for each engine having a similar signature may then be used to determine the condition and the future states of the first engine.

In accordance with a first broad aspect, there is provided a method for evaluating a condition of an engine. Fluid sample data obtained from an engine is received and weights are assigned to different data sets of the fluid sample data. The data sets correspond to one or more classes of materials into which particles of the fluid sample are sorted. A characterizing sample signature of the engine is generated based on the data sets. The sample signature is compared to a plurality of reference signatures obtained from reference engines belonging to a common family with the engine. A selection is made from the reference engines for those having a difference between a corresponding signature and the sample signature below a threshold. Historical engine data of the selected reference engines is output as a basis for evaluating the condition of the engine.

In accordance with another broad aspect, there is provided a system for evaluating a condition of an engine. The system comprises a processing unit; and a non-transitory memory communicatively coupled to the processing unit and comprising computer-readable program instructions executable by the processing unit. The program instructions are executable for receiving fluid sample data of a fluid sample obtained from a first engine; assigning weights to data sets of the fluid sample data, the data sets corresponding to one or more classes of materials into which particles of the fluid sample are sorted; generating a sample signature of the first engine based on the data sets, the sample signature characterizing the first engine as a function of the fluid sample; comparing the sample signature to a plurality of reference signatures obtained from reference engines belonging to a common family with the first engine; selecting ones of the reference engines for which a difference between a corresponding reference signature and the sample signature is below a threshold; and outputting historical engine data of the selected ones of the reference engines as a basis for evaluating the condition of the first engine.

In accordance with yet another broad aspect, there is provided a non-transitory computer readable medium having stored thereon program code executable by a processor for carrying out the methods described herein.

BRIEF DESCRIPTION OF THE DRAWINGS

Further features and advantages of the present invention will become apparent from the following detailed description, taken in combination with the appended drawings, in which.

It will be noted that throughout the appended drawings, like features are identified by like reference numerals.

DETAILED DESCRIPTION

There is described herein methods and systems for evaluating the condition of an engine based on a signature of a fluid sample of the engine, referred to herein as a sample signature. The methods and systems are applicable to any type of engine for which historical data is available from other comparable engines, including external combustion engines and internal combustion engines. The types of internal combustion engines may include, but are not limited to, gas turbine engines such as turboprop engines, turbofan engines, and turboshaft engines. The engine may form part of a vehicle, such as an aircraft, a ship, a train, and an automobile, or be used for other applications, such as power plants, wind turbines, and damns. The fluid sample obtained from the engine may be any type of fluid, such as a lubricant, which may be filtered for particles. In some embodiments, the fluid sample is engine oil.

Figure 1:
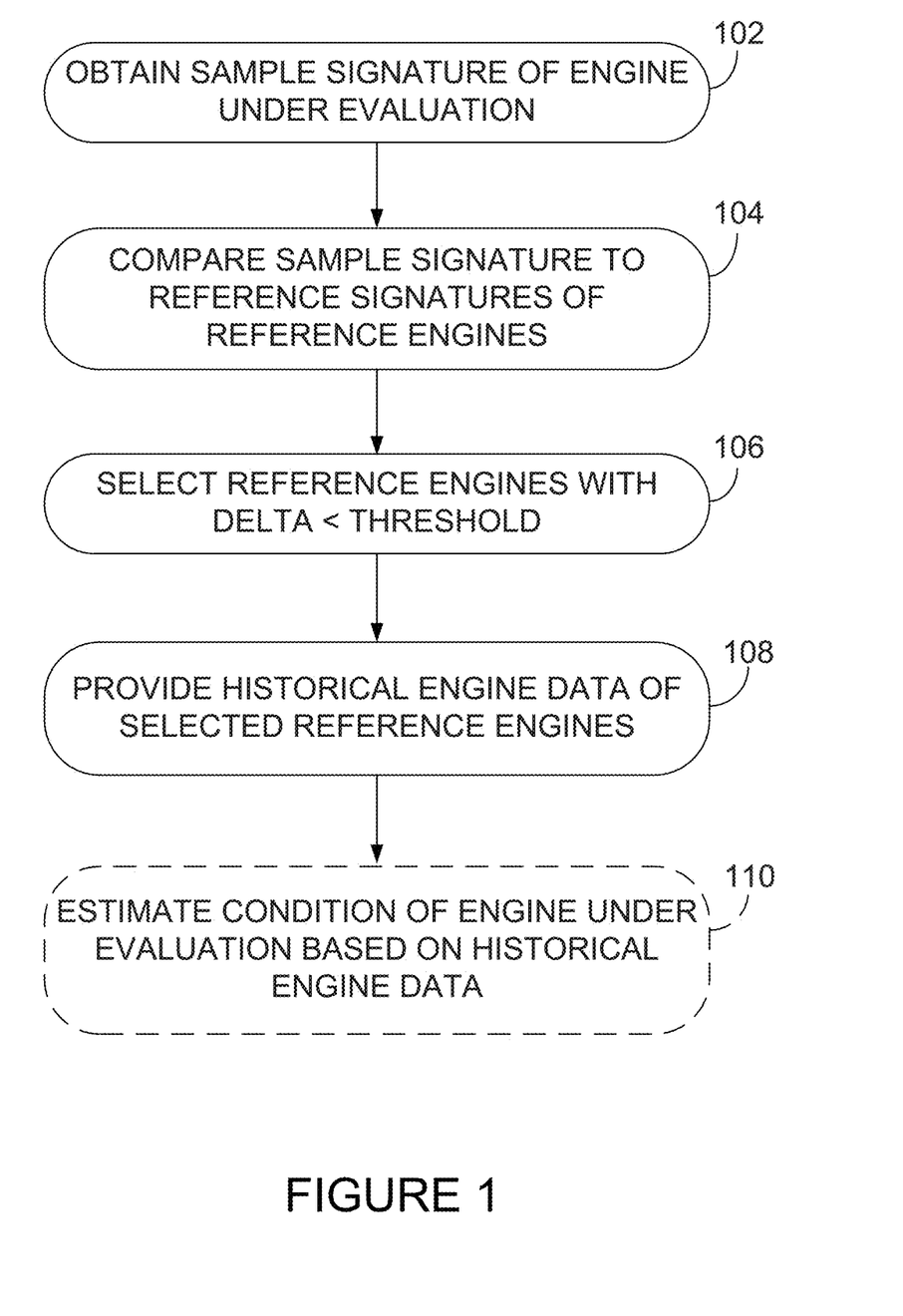
FIG. 1 is a flowchart of an exemplary method for evaluating a condition of an engine.

FIG. 1 refers to a method for evaluating the condition of an engine. At 102, a sample signature of an engine under evaluation, referred to herein as a first engine, is obtained. In some embodiments, obtaining the sample signature comprises receiving a data signal having the sample signature therein. In some embodiments, obtaining the sample signature comprises retrieving the sample signature from a storage medium.

Figure 2:
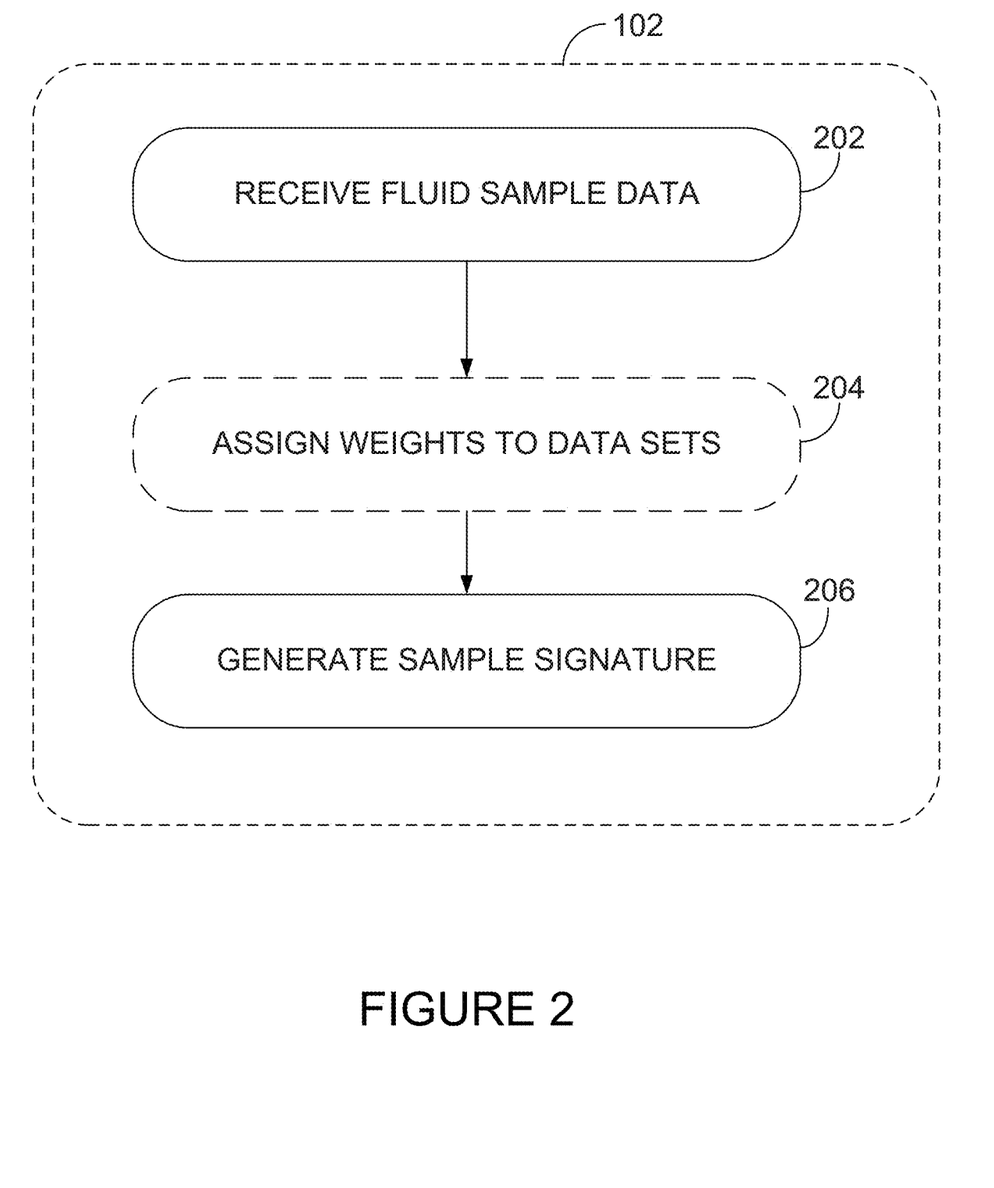
FIG. 2 is a flowchart of an exemplary method for obtaining a sample signature of an engine.

In some embodiments, obtaining the sample signature comprises generating the sample signature from data representative of a fluid sample, as illustratively shown in FIG. 2. At 202, fluid sample data is received. The fluid sample data is from the analysis of a fluid sample obtained for the first engine. For example, in the case of a fluid sample from an aircraft engine, the fluid sample may be collected by an aircraft operator. More than one sample may be obtained from the first engine. A relatively small amount of fluid (e.g., 25 mL or less) may be sufficient. The amount of fluid sample obtained may be selected in order to obtain a certain number of particles. For example, it may be known or expected that a given engine should have a certain density of particles in the fluid after a certain number of operating hours. The volume of fluid sample obtained may thus be determined in order to obtain an optimal quantity of particles. The frequency of sampling may be determined based on the operating hours per year, the maturity of the engine, the typical behavior of the engine type and/or the history of unscheduled engine removal for that engine type, for example.

The fluid sample may be obtained and prepared using any suitable method. The particles may be identified as coming from one or more engine components that shed such particles, such as bearings, baffles, carbon seals, magnetic seals, and gears. Particles may also be identified as a result of two or more material interactions, such as two materials found on a single component or on two separate components, whereby contact occurs through normal or abnormal operation.

Preparation of the sample may involve filtering, which may be performed using various techniques. For example, a collected fluid sample may be filtered using a very fine filter, such as a 0.22 µm filter, in order to filter out even very small particles (e.g., particles sized as small as 0.5 µm in diameter or smaller). Using such a filter, a sample of about 25 mL may produce a surface sample of about 16 mm in diameter. The particles obtained may range in size from about 0.5 µm to about 1600 µm, for example, although smaller or larger particles may also be obtained. The volume of fluid sample filtered and the size of the sample prepared may vary, such as according to the number of particles in the fluid. The volume of fluid sample that is filtered may be determined based on the type of engine and/or the expected normal levels of particles in the fluid. In some examples, the obtained density of particles may be 500 particles per mm$^2$, which may be a density that can be used to reduce or avoid particles overlapping.

Each particle of the sample may be analyzed to determine chemical composition. A scanning electron microscope (SEM) equipped to perform x-ray spectroscopy may be used for this analysis, although any other suitable methods may also be used. A subset of the particles (e.g., 10% or less) may be analyzed while ensuring a good representation of the whole sample is captured. The analysis of the subset may be normalized to reflect the result for the full sample. For an average fluid sample, about 1500 to 2000 particles may be analyzed. Suitable image analyzer software, such as those conventionally used with SEM, may be used to collect data about particle composition. Analysis of each particle may produce a respective set of data for that particle, for example there may be up to 70 data points for each particle, the data describing various features of the particle (e.g., size, shape and composition, among others). In some embodiments, a particle feature may refer to a material interaction, as described in U.S. patent application Ser. No. 15/055,102, the contents of which are hereby incorporated by reference. Other specific properties associated with a particle or a group of particles found in the fluid sample may also be used.

Figure 3A:
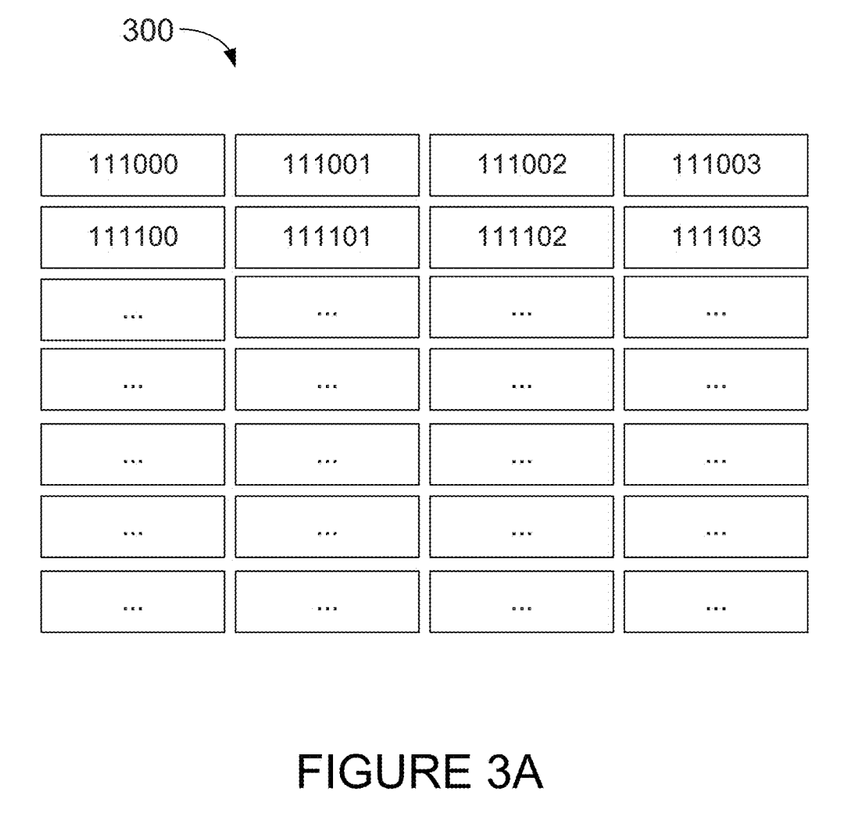
FIG. 3A is an example of a set of classes of materials.
Figure 3B:
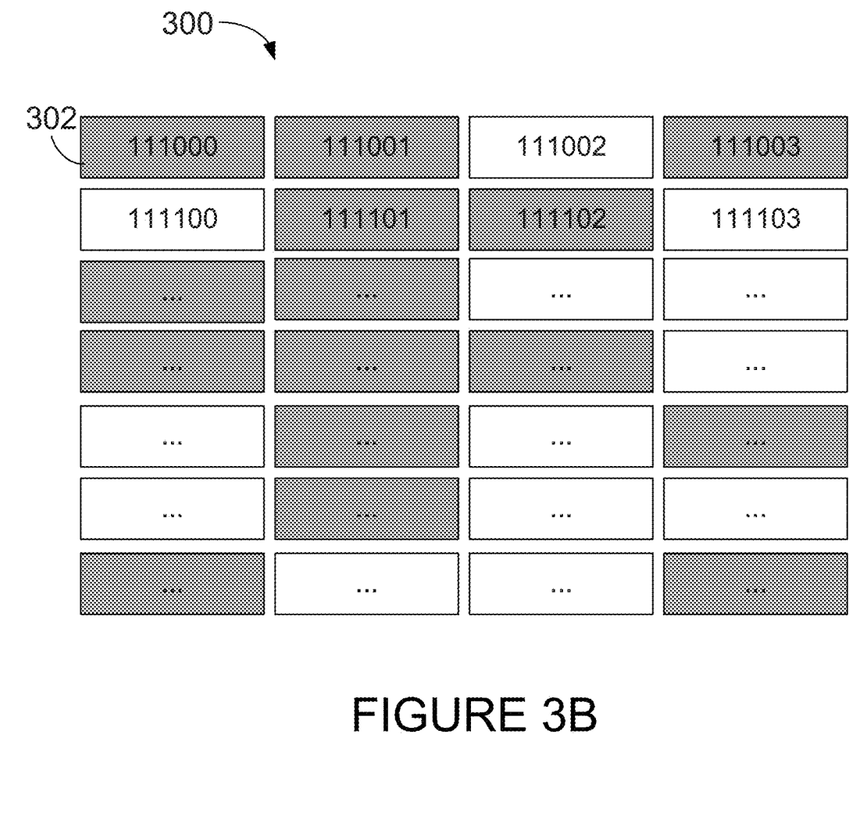
FIG. 3B is an example of a first grouping of the classes of FIG. 3A.

Particles may be sorted into classes of materials. Each class corresponds to a material of a specific chemical composition, i.e. a specific alloy or an interaction of two or more materials, with a given particle shape and particle size range. An example class is stainless steel 18-8 having a particle size of 0.5 to 2.5 µm with an aspect ratio smaller than 5. Other class definitions will be readily understood. FIG. 3A illustrates an example of a plurality of classes 300 of materials, where each class 300 is assigned a class number for illustrative purposes. Values may be calculated for all classes 300. For any given engine, only some of the classes 300 may be applicable, as illustrated in FIG. 3B where classes 302 are applicable to the first engine. In some embodiments, values are only calculated for selected classes 302. Using the example of FIG. 3B, a sample signature for the first engine is composed of the values associated with each one of classes 302.

Figure 3C:
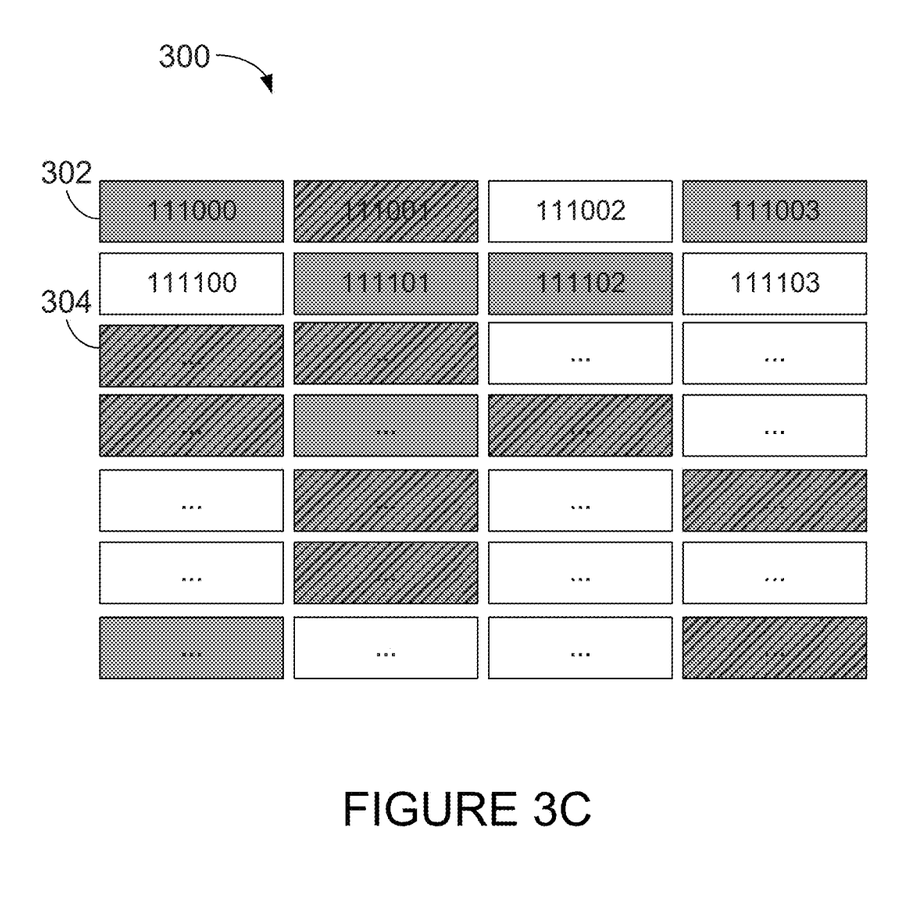
FIG. 3C is an example of two groupings of the classes of FIG. 3A.
Figure 3D:
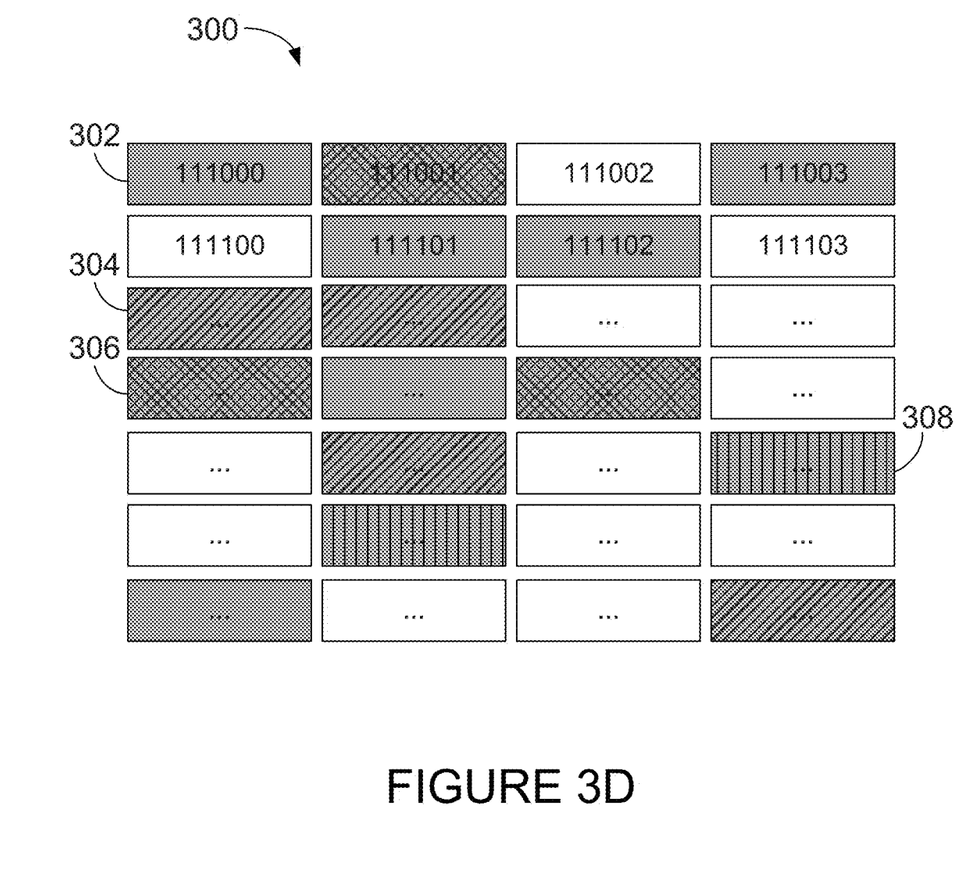
FIG. 3D is an example of four groupings of the classes of FIG. 3A.

In some embodiments, classes 300 are grouped into data sets so as to assign weights thereto, as per step 204 for FIG. 2. Classes 300 may be grouped in various ways. For example, one or more of the applicable classes 302 for the first engine may be associated with a known failure mode and/or with a critical component of the engine, while others may not. These classes 404 may be set apart from the others 302, as illustrated in FIG. 3C. The unassociated classes 304 may themselves form a data set. The associated classes 302 may be further separated into different data sets as a function of a criticality and/or a uniqueness of the failure mode to which each class is associated. For example, a failure resulting in inflight shut down is more critical than a failure resulting in lower operational efficiency and thus these classes may be provided in different data sets. In another example, a class having six failure modes associated thereto would be grouped separately from a class having a single failure mode associated thereto. FIG. 3D illustrates an example with classes 300 separated into four data sets 302, 304, 306, 308.

Once the data sets are defined, classes may be ranked accordingly, using any ranking system. For example, the four data sets 302, 304, 306, 308 may be ranked with four separate weight categories, such as very low weight, low weight, medium weight, and high weight. Data sets for failure modes of higher criticality are assigned higher weights than data sets for failure modes of lower criticality. Data sets for a greater number of failure modes are assigned lower weights than data sets for a lower number of failure modes. The classes that form each data set, the number of data sets, and the weight associated with each data set may vary.

In some embodiments, a total weight $W_T$ for a data set is composed of a predetermined weight $W_p$ and a variable weight $W_c$. The predetermined weight $W_p$ may be fixed and independent of the data points forming the data sets. For example, data sets for particles shed from bearing materials may be assigned a predetermined weight W. The variable weight $W_c$ may be dependent on the data points forming the data sets. For example, a variable weight $W_c$ may be based on a deviation of the data point value from an average value for the data point. The variable weight $W_c$ may be calculated or may be obtained from a look-up table, using previously defined values assigned to various ranges of deviation.

Referring back to FIG. 2, at 206, the sample signature is generated and associated with the first engine. Note that in some embodiments, the sample signature is generated simply with the data sets and without any weights assigned thereto. The weights may be assigned at a later stage in the method of FIG. 1, as will be explained in more detail below. The sample signature may be composed of one or more numerical values, depending on the number of data sets forming the signature.

Returning to FIG. 1, at 104 the sample signature is compared to reference signatures of reference engines from a common engine family. The reference signatures are obtained using a similar method as that used to obtain the sample signature. In some embodiments, the reference signatures are received or retrieved from a storage medium. Alternatively, reference signatures may be obtained using a method analogous as that illustrated in FIG. 2 for the sample signature.

The reference engines used for the comparison form part of a common family with the first engine. An engine family may be defined by any engine characteristic, such as type, model, operating principle, configuration, use, performance, thrust, torque, speed, power, etc. An engine family may also be defined by two or more engine features. For example, a family may correspond to turboprop engines, or turboprop engines in use in aircraft, or turboprop engine in use in aircraft and weighing between 150 and 450 kg. In another example, a family may correspond to a specific model or series, such as the PT-6 Series from Pratt & Whitney Canada. In some embodiments, a family may comprise sub-families, i.e. the family has at least one common engine characteristic and each sub-family has at least one additional common engine characteristic. Various combinations may be used.

Comparing the sample signature to the reference signatures, as per step 104, comprises determining a difference, or delta, between the sample signature and each reference signature from the common family. In some embodiments, the delta corresponds to a single numerical value. For example, if the sample signature has a single data set represented by A and a first reference signature has a single data set represented by B, then the delta is A−B. When the signatures are composed of a plurality of data sets, such as $(A_1, A_2)$, for the sample signature and $(B_1, B_2)$ for the first reference signature, then the delta is composed of an equal number of data sets, such as $(A_1-B_1, A_2-B_2)$. Therefore, the delta may be composed of any number of data sets.

In some embodiments, the sample signature and the reference signatures are unweighted and weights are considered at the time of determining the delta. For example, the following formula may be used to determine the delta with each reference signature:

$$\sum_{i=1}^{n} \frac{W_{Ti}(D_{Ei} - D_{Ci})^2}{D_{Ei} + D_{Ci}}$$

where n is a number of data sets in sample signature, $W_n$ is the total weight for a data set i, $D_{Ei}$ is a value of a given data set of the fluid sample from the first engine, and $D_{Ci}$ is a value of a given data set of a fluid sample from a reference engine of the corresponding reference signature.

The delta is representative of how similar the pattern of the first engine is to the pattern of any of the reference engines from the common engine family. At 106, reference engines having a delta with the first engine that is less than or equal to a threshold are selected. The threshold may be determined through data analysis.

At 108, historical engine data associated with the reference engines having the delta less than or equal to the threshold is provided as a basis for evaluating the condition of the first engine.

In some embodiments, historical data corresponds to one or more events associated with each reference engine. For example, the event may be a total number of operating hours for each reference engine. In another example, the event may be a number of operating hours until a specific occurrence, such as a reduction in efficiency of the reference engine by 10%, 25%, and/or 50%, a need for an oil change or a maintenance, or an unplanned engine breakdown. Some or all of the events associated with each reference engine may be provided as part of the historical data.

In some embodiments, the historical data is presented as one or more averages for all reference engines having a delta less than or equal to the threshold. For example, If 50 reference engines are selected, the historical data of all 50 reference engines may be compiled together and presented in terms of the following averages: average total operating hours, average operating hours until a specific occurrence, average efficiency of engines after a specific number of operating hours, etc.

In some embodiments, the historical data is presented as a percentage of selected engines matching one or more events. For example, out of 50 reference engines selected, i.e. showing a similar signature, the historical data may be presented as: 100% operated 200 hours without any problems, 91% operated 500 hours without any problems, 73% operated 600 hours without any problems, 10% operated 750 hours without any problems. Other events, such as those stated above or others, may also be used in this format.

In some embodiments, the method further comprises estimating the condition of the first engine based on the historical data, as per 110. Estimating the condition may comprise assigning a rating to the first engine. Various types of engine rating systems may be used, and comprise any number of rating levels, such as two, three, four, and more. The ratings may be associated with an expected time until maintenance, or an expected time until breakdown. The rating may be determined using only the historical data of the reference engines, or a combination of historical data of the reference engines and historical/current data of the first engine. For example, if the expected time until maintenance is 600 hours, the probability of achievement will be 73% based on the reference engines. Other rating systems may readily apply.

Figure 4:
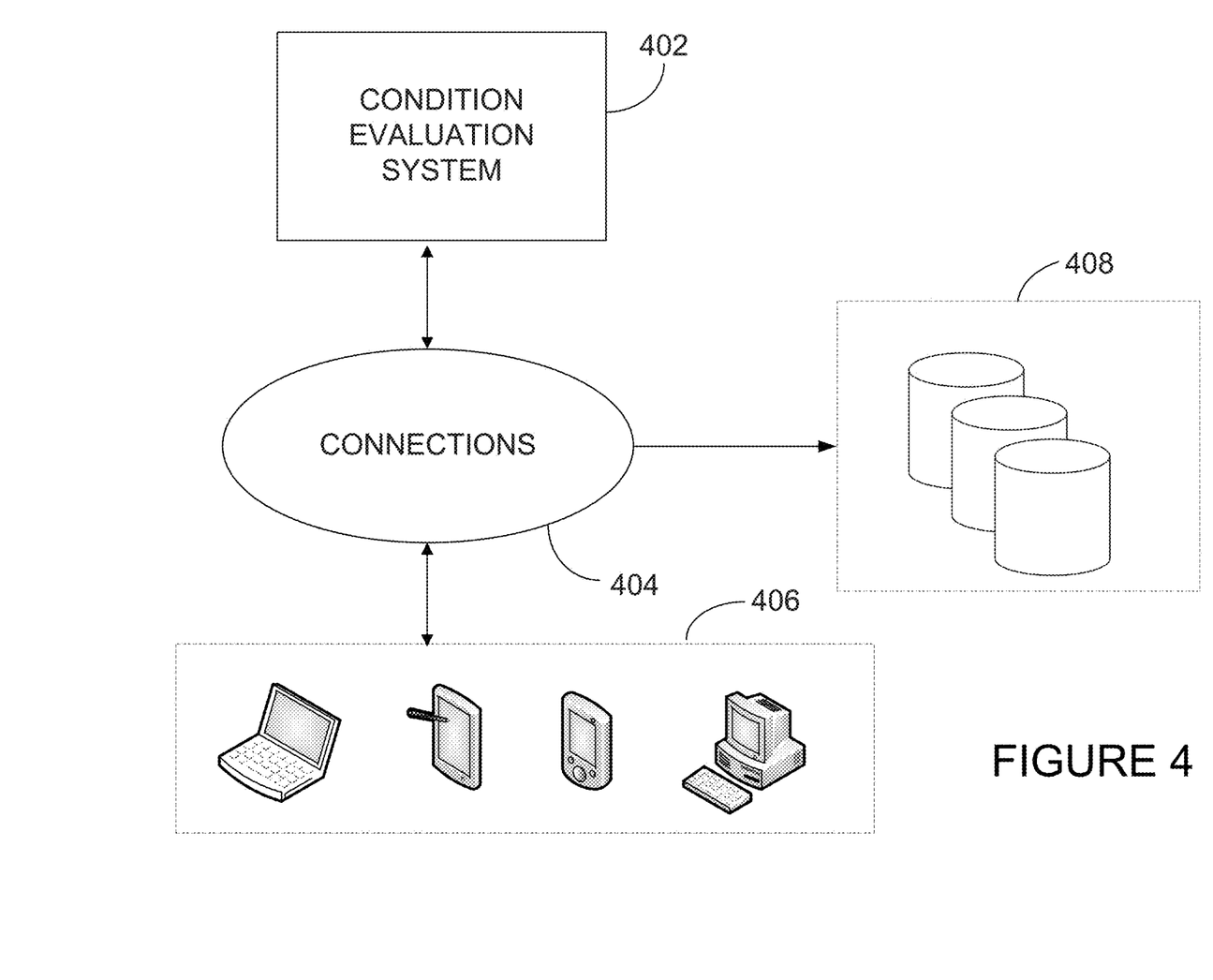
FIG. 4 is a diagram illustrating an exemplary system for evaluating the condition of an engine.

Referring now to FIG. 4, a system for evaluating engine condition will now be described. The system 402, may be accessible remotely from any one of a plurality of devices 406 over connections 404. The connections 404 may comprise wire-based technology, such as electrical wires or cables, and/or optical fibers. The connections 504 may also be wireless, such as RF, infrared, Wi-Fi, Bluetooth, and others. Connections 504 may therefore comprise a network, such as the Internet, the Public Switch Telephone Network (PSTN), a cellular network, or others known to those skilled in the art. Communication over the network may occur using any known communication protocols that enable devices within a computer network to exchange information. Examples of protocols are as follows: IP (Internet Protocol), UDP (User Datagram Protocol), TCP (Transmission Control Protocol), DHCP (Dynamic Host Configuration Protocol), HTTP (Hypertext Transfer Protocol), FTP (File Transfer Protocol), Telnet (Telnet Remote Protocol), SSH (Secure Shell Remote Protocol). The devices 406 may comprise any device, such as a personal computer, a tablet, a smart phone, or the like, which is configured to communicate over the connections 404. In some embodiments, the engine condition evaluation system 402 may itself be provided directly on one of the devices 406, either as a downloaded software application, a firmware application, or a combination thereof.

One or more databases 408 may be integrated directly into the system 402 or any one of the devices 406, or may be provided separately therefrom (as illustrated). In the case of a remote access to the databases 408, access may occur via connections 404 taking the form of any type of network, as indicated above. The various databases 408 described herein may be provided as collections of data or information organized for rapid search and retrieval by a computer. The databases 408 may be structured to facilitate storage, retrieval, modification, and deletion of data in conjunction with various data-processing operations. The databases 408 may be any organization of data on a data storage medium, such as one or more servers. The databases 408 illustratively have stored therein raw data representing a plurality of features of the particles filtered from the fluid sample obtained, the features being for example physical characteristics and chemical composition. The databases 408 may also have stored thereon specific chemical composition data from particle analysis, sample signatures, reference signatures, weights, deltas, historical data, condition ratings, and the outcomes of the evaluation of the condition of engines.

Figure 5:
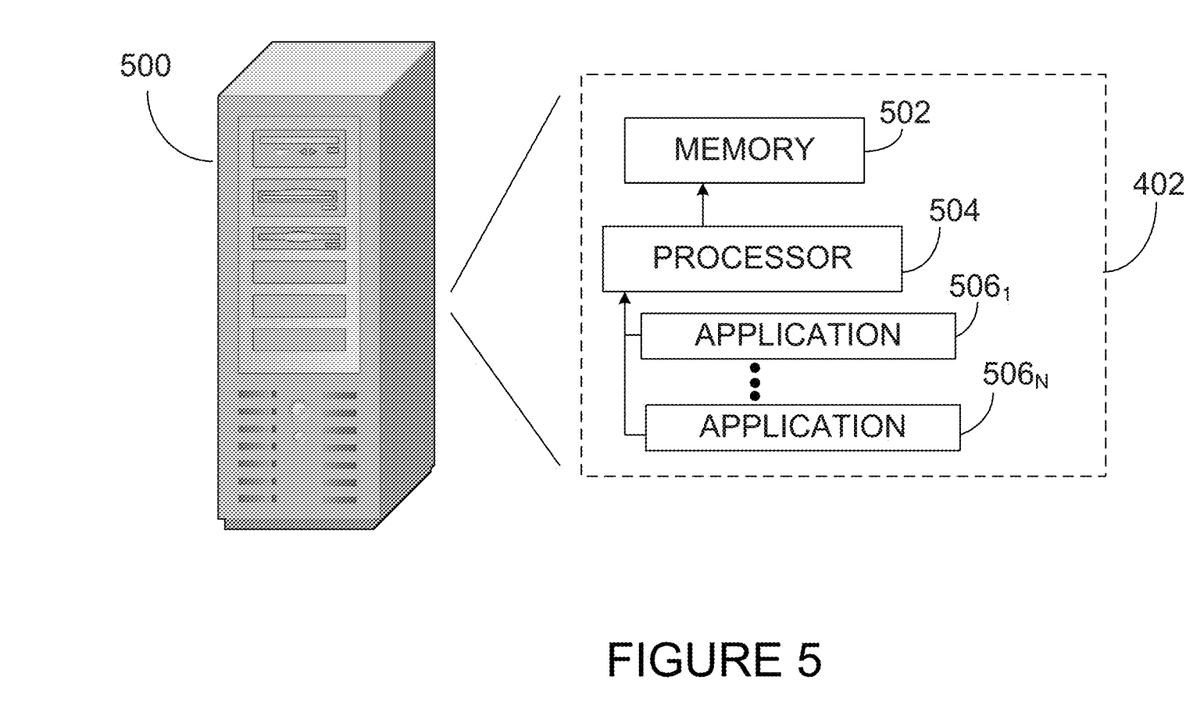
FIG. 5 is an exemplary embodiment of the condition evaluation system.

As shown in FIG. 5, the system 402 illustratively comprises one or more server(s) 500. The server 500 may be accessed by a user, such as a technician or a lab employee, using one of the devices 406, or directly on the system 402 via a graphical user interface. The server 500 may comprise, amongst other things, a plurality of applications $506_1$ . . . $506_n$ running on a processor 504 coupled to a memory 502. It should be understood that while the applications $506_1$ . . . $506_n$ presented herein are illustrated and described as separate entities, they may be combined or separated in a variety of ways.

The memory 502 accessible by the processor 504 may receive and store data. The memory 502 may be a main memory, such as a high speed Random Access Memory (RAM), or an auxiliary storage unit, such as a hard disk, a floppy disk, or a magnetic tape drive. The memory 502 may be any other type of memory, such as a Read-Only Memory (ROM), or optical storage media such as a videodisc and a compact disc. The processor 504 may access the memory 502 to retrieve data. The processor 504 may be any device that can perform operations on data. Examples are a central processing unit (CPU), a front-end processor, a microprocessor, and a network processor. The applications $506_1$ . . . $506_n$ are coupled to the processor 504 and configured to perform various tasks. An output may be transmitted to devices 506.

Figure 6:
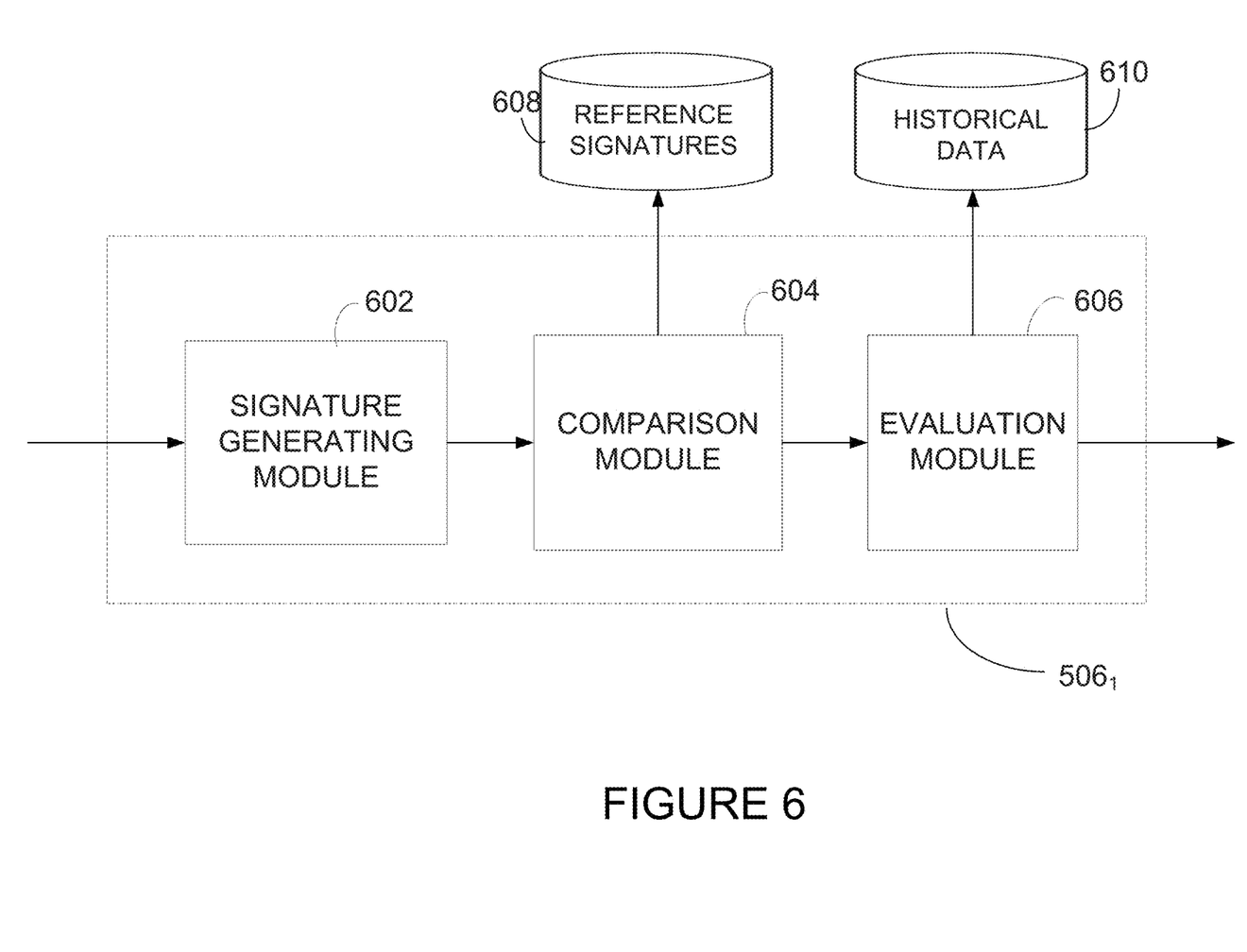
FIG. 6 is an exemplary embodiment of an application running on the system of FIG. 5.

FIG. 6 is an exemplary embodiment of an application $506_1$ running on the processor 504. The application $506_1$ illustratively comprises a signature generating module 602, a comparison module 604, and an evaluation module 606. The signature generating module 602 may be configured to simply receive a sample signature or retrieve it from a storage medium, such as memory 502. In some embodiments, the signature generating module 602 is configured to generate the signature in accordance with the method of FIG. 2, or another signature generating method. For example, the fluid sample data may be received or retrieved by the signature generating module 602 either as a set of classes or as separate particle data that is then grouped into classes by the signature generating module 602. The sample signature is transmitted to the comparison module 604 from the signature generating module 602, either with weights having been applied thereto or without.

The comparison module 604 is configured to compare the sample signature to one or more reference signatures from the reference engines, as per step 104 of FIG. 1. Reference signatures may be retrieved from a database 608 of reference signatures, which may be provided in memory 502 or separately therefrom. The comparison module 604 may also be configured to select reference engines for which the delta with the sample signature is less than the threshold, and provided identification of the selected reference engines to the evaluation module 606.

The evaluation module 606 may be configured to retrieve historical data for the selected reference engines from a database 610 of historical data, which may be provided in memory 502 or separately therefrom. The evaluation module 606 may be configured to provide the historical data as output to a graphical user interface (GUI), for example on any one of devices 406, to a user. The evaluation module 606 may also be configured to estimate the condition rating of the first engine based on the historical data and output the condition rating to the GUI of any one of devices 406.

The application $506_1$ may be configured to receive input via the GUI of devices 406 at one or more steps of the method. For example, the application $506_1$ may receive input instructions for retrieving fluid sample data and/or the sample signature of the first engine. Instructions may also be received for assigning data to classes, grouping classes into data sets, assigning weights to the data sets, selecting weight values, selecting threshold values for the delta, and selecting historical data from selected reference engines. In some embodiments, the application $506_1$ is configured to perform the method of FIG. 1 automatically without any additional instructions once the fluid sample data and/or sample signature has been provided thereto.

In some embodiments, a non-transitory computer readable medium having stored thereon program code executable by a processor for carrying out the methods described herein and illustrated in application $506_1$ may be provided.

The above description is meant to be exemplary only, and one skilled in the relevant arts will recognize that changes may be made to the embodiments described without departing from the scope of the invention disclosed. For example, the blocks and/or operations in the flowcharts and drawings described herein are for purposes of example only. There may be many variations to these blocks and/or operations without departing from the teachings of the present disclosure. For instance, the blocks may be performed in a differing order, or blocks may be added, deleted, or modified.

While illustrated in the block diagrams as groups of discrete components communicating with each other via distinct data signal connections, it will be understood by those skilled in the art that the present embodiments are provided by a combination of hardware and software components, with some components being implemented by a given function or operation of a hardware or software system, and many of the data paths illustrated being implemented by data communication within a computer application or operating system. The structure illustrated is thus provided for efficiency of teaching the present embodiment. The present disclosure may be embodied in other specific forms without departing from the subject matter of the claims. Also, one skilled in the relevant arts will appreciate that while the systems, methods and computer readable mediums disclosed and shown herein may comprise a specific number of elements/components, the systems, methods and computer readable mediums may be modified to include additional or fewer of such elements/components. The present disclosure is also intended to cover and embrace all suitable changes in technology. Modifications which fall within the scope of the present invention will be apparent to those skilled in the art, in light of a review of this disclosure, and such modifications are intended to fall within the appended claims.

The invention claimed is:

1. A method for evaluating a condition of an engine, the method comprising:
    receiving fluid sample data of a fluid sample obtained from a first engine;
    assigning weights to data sets of the fluid sample data, the data sets corresponding to one or more classes of materials into which particles of the fluid sample are sorted;
    generating a sample signature of the first engine based on the data sets, the sample signature characterizing the first engine as a function of the fluid sample;
    comparing the sample signature to a plurality of reference signatures obtained from reference engines belonging to a common family with the first engine;
    selecting ones of the reference engines for which a difference between a corresponding reference signature and the sample signature is below a threshold; and
    outputting historical engine data of the selected ones of the reference engines as a basis for evaluating the condition of the first engine.

2. The method of claim 1, wherein assigning weights to data sets comprises assigning a total weight to each data set, the total weight composed of a predetermined weight and a variable weight.

3. The method of claim 2, wherein the variable weight is based on a deviation of a given value for a given data set from an average value for the given data set.

4. The method as claimed in claim 1, wherein the first engine and the reference engines belong to a common family when they correspond to a same engine model.

5. The method of claim 1, wherein outputting historical engine data of the selected ones of the reference engines comprises outputting a total number of operating hours of the selected ones of the reference engines.

6. The method of claim 1, wherein outputting historical engine data of the selected ones of the reference engines comprises outputting which portion of the selected ones of the reference engines ran without any problems for at least one total number of operating hours.

7. The method of claim 1, further comprising estimating the condition of the first engine based on the historical data of the selected ones of the reference engines.

8. The method of claim 1, further comprising evaluating the condition of the first engine based on the historical engine data of the selected ones of the reference engines.

9. The method of claim 8, wherein evaluating the condition of the first engine comprises assigning a rating to the first engine based on the historical engine data of the selected ones of the reference engines.

10. The method of claim 9, wherein the rating is associated with an expected time until maintenance or an expected time until breakdown.

11. A system for evaluating a condition of an engine, the system comprising:
    a processing unit; and
    a non-transitory memory communicatively coupled to the processing unit and comprising computer-readable program instructions executable by the processing unit for:
        receiving fluid sample data of a fluid sample obtained from a first engine;
        assigning weights to data sets of the fluid sample data, the data sets corresponding to one or more classes of materials into which particles of the fluid sample are sorted;
    generating a sample signature of the first engine based on the data sets, the sample signature characterizing the first engine as a function of the fluid sample;
    comparing the sample signature to a plurality of reference signatures obtained from reference engines belonging to a common family with the first engine;
    selecting ones of the reference engines for which a difference between a corresponding reference signature and the sample signature is below a threshold; and
    outputting historical engine data of the selected ones of the reference engines as a basis for evaluating the condition of the first engine.

12. The system of claim 11, wherein assigning weights to different data sets comprises assigning a total weight to each data set, the total weight composed of a predetermined weight and a variable weight.

13. The system of claim 12, wherein the variable weight is based on a deviation of a given value for a given data set from an average value for the given data set.

14. The system as claimed in claim 11, wherein the first engine and the reference engines belong to a common family when they correspond to a same engine model.

15. The system of claim 11, wherein outputting historical engine data of the selected ones of the reference engines comprises outputting a total number of operating hours of the selected ones of the reference engines.

16. The system of claim 11, wherein outputting historical engine data of the selected ones of the reference engines comprises outputting which portion of the selected ones of the reference engines ran without any problems for at least one total number of operating hours.

17. The system of claim 11, wherein the program instructions are further executable for estimating the condition of the first engine based on the historical data of the selected ones of the reference engines.

18. The system of claim 11, wherein the program instructions are further executable for evaluating the condition of the first engine based on the historical engine data of the selected ones of the reference engines.

19. The system of claim 18, wherein evaluating the condition of the first engine comprises assigning a rating to the first engine based on the historical engine data of the selected ones of the reference engines.

20. The system of claim 19, wherein the rating is associated with an expected time until maintenance or an expected time until breakdown.

* * * * *